US011092585B2

(12) United States Patent
Dweik et al.

(10) Patent No.: US 11,092,585 B2
(45) Date of Patent: Aug. 17, 2021

(54) ELECTROCHEMICAL METHOD FOR DETECTION AND QUANTIFICATION OF ORGANIC COMPOUNDS IN WATER

(71) Applicant: Giner, Inc., Newton, MA (US)

(72) Inventors: Badawi M. Dweik, Foxborough, MA (US); Avni A. Argun, Newton, MA (US); Katherine E. Harrison, Arlington, MA (US)

(73) Assignee: GINER, INC., Newton, MA (US)

( * ) Notice: Subject to any disclaimer, the term of this patent is extended or adjusted under 35 U.S.C. 154(b) by 0 days.

(21) Appl. No.: 16/287,431

(22) Filed: Feb. 27, 2019

(65) Prior Publication Data

US 2020/0025740 A1 Jan. 23, 2020

Related U.S. Application Data (60) Provisional application No. 62/635,736, filed on Feb. 27, 2018.

(51) Int. Cl.
| | | |
|---|---|---|
| *G01N 33/18* | (2006.01) | |
| *G01N 27/327* | (2006.01) | |
| *G01N 27/42* | (2006.01) | |

(52) U.S. Cl.
CPC ....... *G01N 33/1826* (2013.01); *G01N 27/327* (2013.01); *G01N 27/423* (2013.01); *G01N 33/1806* (2013.01); *G01N 33/1886* (2013.01)

(58) Field of Classification Search
None
See application file for complete search history.

(56) References Cited

U.S. PATENT DOCUMENTS

| | | |
|---|---|---|
| 5,223,118 A | 6/1993 | Sonnenberg et al. |
| 5,399,247 A | 3/1995 | Carey et al. |
| (Continued) | | |

FOREIGN PATENT DOCUMENTS

| | | |
|---|---|---|
| CN | 102866186 B | 8/2014 |
| EP | 0470649 B1 | 6/1999 |
| (Continued) | | |

OTHER PUBLICATIONS

Machine translation to English of CN 102866186 B (Year: 2014).*
(Continued)

*Primary Examiner* — J. Christopher Ball
(74) *Attorney, Agent, or Firm* — Kriegsman & Kriegsman (57) ABSTRACT

Method and system for detection and quantification of oxidizable organics in water. The method involves the partial electrolytic decomposition of the oxidizable organics in a short time frame, preferably less than five seconds, and does not involve the use of toxic reagents. The system includes an electrochemical sensor probe that, in turn, includes a boron-doped diamond microelectrode array. The system additionally includes an electronic transducer and a computing device. The system utilizes an analysis technique to convert sensor signal to a result that can be correlated with COD or BOD values obtained by standard methods. The method and system are particularly suitable for, but not limited to, use in monitoring of water quality at wastewater treatment plants. By employing the method before and after adding aerobic microorganisms to the sample, the method may be used to distinguish biologically oxidizable organics from total oxidizable organics.

20 Claims, 9 Drawing Sheets

(56) References Cited

U.S. PATENT DOCUMENTS

| | | | |
|---|---|---|---|
| 6,565,725 | B2 | 5/2003 | Sugaya et al. |
| 8,177,949 | B2 | 5/2012 | Pickles et al. |
| 8,919,573 | B2 | 12/2014 | Capehart |
| 8,999,173 | B2 | 4/2015 | Schwartzel et al. |
| 2010/0294672 | A1* | 11/2010 | Gahr .................. G01N 33/1806 205/786 |
| 2012/0058508 | A1 | 3/2012 | Bhattacharya |

FOREIGN PATENT DOCUMENTS

| | | | |
|---|---|---|---|
| EP | 1055926 A2 | 11/2000 | |
| WO | WO-2013100101 A1 * | 7/2013 | ......... G01N 33/1846 |

OTHER PUBLICATIONS

International Search Report dated Jun. 10, 2019, in PCT Application No. PCT/US19/19824, the corresponding PCT application to the present application.

Written Opinion dated Jun. 10, 2019, in PCT Application No. PCT/US19/19824, the corresponding PCT application to the present application.

Kondo et al., "Direct Determination of Chemical Oxygen Demand by Anodic Decomposition of Organic Compounds at a Diamond Electrode," Analytical Chemistry, 86:8066-8072 (2014).

Bourgeois et al., "On-line monitoring of wastewater quality: a review," Journal of Chemical Technology and Biotechnology, 76:337-348 (2001).

Fujishima et al., "Fundamental and Applied Aspects of Diamond Electrodes," Diamond Electrochemistry, pp. 556-574, B.V. Elsevier, Tokyo, Japan (2005).

Furuta et al., "Application of Diamond Electrodes for Water Disinfection," Diamond Electrochemistry, pp. 525-542, B.V. Elsevier, Tokyo, Japan (2005).

Argun et al., "Highly sensitive detection of urinary cadmium to assess personal exposure," Analytica Chimica Acta, 773: 45-51 (2013).

Denuault et al., "Direct determination of diffusion coefficients by chronoamperometry and microdisk electrodes," J. Electroanal. Chem., 308: 27-38 (1991).

Operations Manual for 910 COD Colorimeter, Xylem, Inc., Yellow Springs, OH (2012).

https://www.sbir.gov/sbirsearch/detail/1159847; SBIR award details web page entitled "Real-Time Sensor for Continuous On-Line Monitoring of Wastewater Quality" (2016).

https://www.sbir.gov/sbirsearch/detail/815433; SBIR award details web page entitled "Real-Time Sensor for Continuous On-Line Monitoring of Wastewater Quality" (2014).

* cited by examiner

ELECTROCHEMICAL METHOD FOR DETECTION AND QUANTIFICATION OF ORGANIC COMPOUNDS IN WATER

CROSS-REFERENCE TO RELATED APPLICATIONS

The present application claims the benefit under 35 U.S.C. 119(e) of U.S. Provisional Patent Application No. 62/635,736, inventors Badawi Dweik et al., filed Feb. 27, 2018, the disclosure of which is incorporated herein by reference.

FEDERALLY SPONSORED RESEARCH OR DEVELOPMENT

This invention was made with government support under W56HZV-16-C-0020 awarded by the United States Army and under WC-133R-16-CN-0045 awarded by the National Oceanic and Atmospheric Administration. The government has certain rights in the invention.

BACKGROUND OF THE INVENTION

The present invention relates generally to the detection and quantification of organic compounds in water samples and relates more particularly to a new method and system for detecting and quantifying organic compounds in water samples.

The presence of pollutants in water sources (e.g., rivers, lakes, industrial wastewater, etc.) threatens the well-being and safety of the overwhelming majority of all living organisms. As a result, several techniques have been devised to detect and to quantify various types of pollutants in water. In particular, one type of water pollutant of heightened interest is the class of organic compounds (i.e., carbon-containing compounds). Accordingly, through the years, a number of techniques have been employed to detect and to quantify organic compounds in water.

One such technique for detecting and quantifying organic compounds in water is a test commonly referred to as the "Biological Oxygen Demand test" (also commonly known as "Biological Oxygen Demand" or "BOD"). Simply stated, Biological Oxygen Demand measures the amount of dissolved oxygen in a water sample that is needed by aerobic microorganisms in the water sample to oxidize organic matter present in the water sample at a particular temperature over a specific time period. In practice, to determine Biological Oxygen Demand, the dissolved oxygen concentration of a water sample is measured. Next, the sample is spiked with a quantity of aerobic microorganisms and then is allowed to incubate in a darkroom at a particular temperature for a certain period of time (typically five days at 20° C.). Then, after the incubation period, the dissolved oxygen concentration is measured once again. The dissolved oxygen concentrations before and after the incubation period, together with a dilution factor, are then used to generate a BOD value, which is most commonly expressed in milligrams of oxygen consumed per liter of sample during five days of incubation at 20° C.

Although the Biological Oxygen Demand test has been in use for approximately 100 years, this technique suffers from a number of shortcomings. For one thing, the test is time-consuming and labor-intensive, typically requiring an incubation period of five days, various manipulations, and specialized equipment. As a result, the Biological Oxygen Demand test has no practical viability as an on-site, real-time evaluative technique. Moreover, the Biological Oxygen Demand test is limited to organic matter that is oxidizable (i.e., digestible) by the aerobic microorganisms that are present in the water sample. As a result, the presence of organic compounds in the sample that are not digestible by the aerobic microorganisms is not reflected in the determined BOD value. Furthermore, the Biological Oxygen Demand test is adversely affected by toxic substances present in the water sample that harm or kill the aerobic microorganisms in the sample.

Another well-known technique for detecting and quantifying organic compounds in water is a test commonly referred to as the "Chemical Oxygen Demand test" (also commonly known as "Chemical Oxygen Demand" or "COD"). Chemical Oxygen Demand is a measure of the capacity of water to consume oxygen during the decomposition of organic matter. Chemical Oxygen Demand is based on the principle that most organic compounds can be completely oxidized using a strong oxidizing agent under acid conditions. In practice, Chemical Oxygen Demand is typically measured using a standardized laboratory assay in which a water sample is incubated with potassium dichromate under acid conditions at a specific temperature for a particular period of time to completely oxidize all organic compounds contained therein. After the incubation period is complete and all organic matter has been decomposed, the amount of organic matter that was present can be indirectly measured by determining how much dichromate was consumed in the decomposition of the organic matter. The determination of how much dichromate was consumed can be accomplished by noting the change in absorbance of the sample. The samples absorb at particular wavelengths due to the color of trivalent chromium ($Cr^{3+}$) and hexavalent chromium ($Cr^{6+}$). Consequently, one can quantify the amount of trivalent chromium in a sample after digestion by measuring the absorbance of the sample at an appropriate wavelength and then by comparing the measured absorbance to standards.

Chemical Oxygen Demand possesses certain advantages over Biological Oxygen Demand. For example, whereas Biological Oxygen Demand is impacted by the presence in the sample of a material that is harmful to the digesting microorganism, Chemical Oxygen Demand is not similarly impacted. Also, Chemical Oxygen Demand can be performed in a significantly shorter time frame than Biological Oxygen Demand can be performed (i.e., approximately two to three hours for COD vs. five days for BOD). Nevertheless, despite the fact that Chemical Oxygen Demand can be performed in a shorter time frame than Biological Oxygen Demand, the time required to perform Chemical Oxygen Demand is still too long to preclude its use as a real-time evaluative technique. In addition, like Biological Oxygen Demand, Chemical Oxygen Demand requires specialized equipment and processing that preclude its practical use as an on-site technique. Moreover, Chemical Oxygen Demand additionally suffers from the limitation that the chromium and other chemicals that are used produce hazardous waste that requires special disposal. Furthermore, because Chemical Oxygen Demand is not limited to measuring organic matter that is digestible by microorganisms, Chemical Oxygen Demand is incapable of distinguishing biodegradable organic pollutants from non-biodegradable organic pollutants.

Another technique for detecting and quantifying organic compounds in water is disclosed in Kondo et al., "Direct Determination of Chemical Oxygen Demand by Anodic Decomposition of Organic Compounds at a Diamond Electrode," Analytical Chemistry, 86:8066-8072 (2014), which is incorporated herein by reference. The aforementioned Kondo et al. paper discloses an electrochemical technique, denoted therein as "electrochemical oxygen demand" (or "ECOD"). According to Kondo et al., in the practice of ECOD, a highly positive potential (+2.5 V vs Ag/AgCl) was applied to an aqueous electrolyte containing potassium hydrogen phthalate, glucose, and lactic acid or sodium dodecylbenzenesulfonate using a boron-doped diamond (BDD) electrode, and an anodic current corresponding to the complete electrolytic decomposition of these organic compounds was observed. The electric charge for the anodic current observed at the BDD electrode was found to be consistent with the theoretical charge required for the complete electrolytic decomposition of the organic compound to $CO_2$ and was used to calculate COD. According to Kondo et al., this analysis was performed by a simple I-t measurement at constant potential using a BDD electrode, and no calibration was needed.

Optical techniques, such as light absorption spectroscopy and fluorescence spectroscopy, have also been used in water quality monitoring. Unfortunately, however, such optical techniques require expensive equipment for in-situ monitoring of organics. Moreover, there are significant technical hurdles to overcome including the turbidity of samples, the biofouling of probe tips, calibration stability, and interference from irrelevant constituents. For example, light absorption/scattering measurements are often affected by the presence of air bubbles in solutions, which can cause interference to the optical signal and can result in errors. Similarly, a high concentration of suspended particles in the sample can also be a major limiting factor. Moreover, agitation and aeration processes result in significant noise in the data, making the integration of optical methods very difficult.

Additional information regarding the monitoring of water samples is disclosed in Bourgeois et al., "On-line monitoring of wastewater quality: a review," *Journal of Chemical Technology and Biotechnology*, 76:337-348 (2001), which is incorporated herein by reference. In the aforementioned Bourgeois et al. paper, additional techniques, such as Total Organic Carbon (TOC) are also disclosed.

SUMMARY OF THE INVENTION

It is an object of the present invention to provide a new method for detecting and quantifying organic compounds in water samples.

It is another object of the present invention to provide a method as described above that overcomes at least some of the disadvantages associated with existing methods.

Therefore, according to one aspect of the present invention, there is provided a method for detecting and quantifying organic compounds in a water sample, the method comprising the steps of (a) providing a system, the system comprising (i) a probe, the probe comprising a boron-doped diamond microelectrode sensor; (ii) instrumentation to apply potential to the sensor and to measure sensor response; and (iii) instrumentation to convert sensor response to a value indicative of a quantity of electrochemically oxidizable organics present in the water sample; (b) inserting the sensor into the water sample; (c) applying a voltage to the sensor to only partially electrolytically decompose the oxidizable organics present in the water sample; and (d) analyzing the sensor response to the applied voltage to yield a value indicative of the quantity of electrochemically oxidizable organics present in the water sample.

In a more detailed feature of the invention, the voltage may be applied to the sensor for at least as long as needed to elicit a steady-state current response from the sensor.

In a more detailed feature of the invention, the voltage may be applied to the sensor as a three-step voltage profile, in which a first potential may be applied for a first period of time, then a second potential, which may be greater than the first potential, may be applied for a second period of time, and then a third potential, which may be less than the second potential, may be applied for a third period of time.

In a more detailed feature of the invention, the second potential may be applied for at least as long as needed to elicit a steady-state current response from the sensor.

In a more detailed feature of the invention, the second potential may be applied for no more than about 4-5 seconds.

In a more detailed feature of the invention, the voltage applied in the second step may be in a range of 0-3 V.

In a more detailed feature of the invention, the voltage applied in the second step may be in a range of 2-3 V.

In a more detailed feature of the invention, the boron-doped diamond microelectrode sensor may comprise an array of boron-doped diamond microelectrodes.

In a more detailed feature of the invention, the array of boron-doped diamond microelectrodes may comprise a plurality of boron-doped diamond microelectrodes having a diameter in the range of about 5-50 µm and having a spacing of about 50-500 µm.

In a more detailed feature of the invention, the probe may further comprise a counter electrode and a reference electrode.

In a more detailed feature of the invention, the instrumentation to apply potential to the sensor and to measure sensor response may comprise a potentiostat, and the instrumentation to convert sensor response to a value indicative of a quantity of electrochemically oxidizable organics present in the water sample may comprise a computer.

In a more detailed feature of the invention, the method may further comprise, before inserting the sensor into the water sample, the step of adding salt to the water sample to produce a conductivity in the water sample in a range of about 100 µS/cm to 100,0000 µS/cm.

In a more detailed feature of the invention, the method may further comprise repeating the applying and analyzing steps at least one time.

In a more detailed feature of the invention, the method may further comprise, after step (d), spiking the water sample with a quantity of an aerobic microorganism capable of digesting organic compounds, allowing the spiked water sample to sit for a period of time, re-inserting the sensor into the spiked water sample in the event that it had previously been removed, and then repeating steps (c) and (d) for the spiked water sample.

In a more detailed feature of the invention, a series of different potentials may be applied in the second step of the three-step voltage profile to distinguish organic compounds present in the water sample.

In a more detailed feature of the invention, the analyzing step may comprise determining at least one metric based on sensor response and comparing the at least one metric to chemical oxygen demand standards.

In a more detailed feature of the invention, the metric may be the slope (S1) of a charge vs. $t^{1/2}$ plot.

In a more detailed feature of the invention, the metric may be the slope (S2) of an $i/i_{ss}$ vs. $t^{-1/2}$ curve, wherein i is current and $i_{ss}$ is steady state current.

In a more detailed feature of the invention, the metric may be the slope (S3) of a di/dt vs. $t^{-3/2}$ curve.

In a more detailed feature of the invention, the metric may be S1*S2.

In a more detailed feature of the invention, the metric may be S2*S3.

The present invention is also directed at a system for performing the above-described method.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts.

DETAILED DESCRIPTION OF THE INVENTION

The present invention is based, at least in part, on the surprising discovery that, in certain situations, one can detect and quantify organic compounds in a water sample based on only a partial electrolytic decomposition of the organic compounds in the water sample. More specifically, as discussed below in greater detail, in accordance with one embodiment of the present invention, one can detect and quantify organic compounds that are present in a water sample, even with only a partial decomposition of the organic compounds in the sample, by using a boron-doped diamond (BDD) microelectrode, by applying a highly oxidizing positive potential to the sample until a steady state current is obtained and then by analyzing the current/charge as a function of time corresponding to the partial electrolytic decomposition of the organic compounds. As a result, the present method can be performed in as short a period of time as a few seconds (e.g., about 4-5 seconds). This is in stark contrast with the above-described approach of Kondo et al., which requires the complete electrolytic decomposition of organic compounds at a bulk BDD electrode and, as a result, can require as long as two to three hours or longer to perform.

Consequently, the present invention is directed at a novel method and system for detecting and quantifying organic compounds in water samples. According to one embodiment, the system of the present invention may comprise (a) a probe comprising a boron-doped diamond (BDD) microelectrode sensor, a counter electrode, and a reference electrode; (b) instrumentation to apply potential to the sensor and to measure sensor response; and (c) instrumentation to convert sensor response to a determination of a quantity of electrochemically oxidizable organics present in a water sample.

The present invention utilizes a direct electrochemical oxidation approach to provide a simple and rapid analysis of samples via oxidizing species in aqueous solutions. A challenge in performing oxidation in aqueous medium is to avoid water electrolysis and electrode corrosion, both of which strongly interfere with signal response at high applied voltages. A key innovation of the present invention is the use of a sensor platform that includes a boron-doped diamond (BDD) microelectrode, together with the use of novel techniques for processing the measurements obtained therewith.

Figure 1:
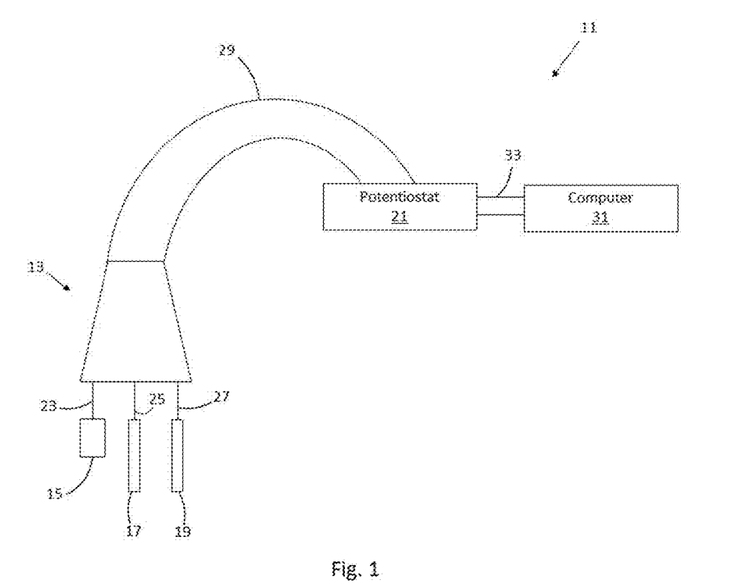
FIG. 1 is a simplified schematic diagram of one embodiment of a system constructed to perform the method of the present invention.

Referring now to FIG. 1, there is shown a simplified schematic diagram of one embodiment of a system constructed according to the present invention for detecting and quantifying organic compounds in a water sample, the system being represented generally by reference numeral 11. Elements or features of system 11 that are not important to an understanding of the invention may be shown in a simplified manner in FIG. 1 or may not be shown at all in FIG. 1 and/or may not be described herein.

System 11 may comprise a probe 13. Probe 13, which may have a distal end that is adapted to be inserted into a volume of a water sample, may comprise a three electrode system comprising a working electrode or sensor 15, a counter electrode 17, and a reference electrode 19.

Working electrode 15 may comprise a boron-doped diamond (BDD) electrode. Boron-doped diamond is a highly efficient electrode material that can oxidize a wide range of organic molecules, including those typically not oxidizable on standard electrode materials. (See Fujishima, A.; Einaga, Y.; Tate, N. R., Tryk, D. A., "Fundamental and Applied Aspects of Diamond Electrodes," *Diamond Electrochemistry*, pages 556-574, B. V. Elsevier, Tokyo, Japan (2005); and Furuta, T.; Rychen, P.; Tanaka, H.; Pupunat, L.; Haenni, W.; Nishiki, Y., "Application of Diamond Electrodes for Water Disinfection," *Diamond Electrochemistry*, pages 525-542, B. V. Elsevier, Tokyo, Japan (2005), both of which are incorporated herein by reference.)

Boron-doped diamond electrodes are also capable of withstanding high oxidation potentials and are resistant to self-oxidation and biofouling. Boron-doped diamond electrodes additionally exhibit a wide potential window (1.0-2.5+V) of water stability, low background currents, and high stability under strongly oxidizing conditions, thereby making boron-doped diamond electrodes well-suited for studying the oxidation profile of complex, multicomponent mixtures.

The boron-doped diamond of working electrode 15 is preferably embodied in the form of a microelectrode, more preferably a microelectrode array. As will be discussed further below, the use of a boron-doped diamond microelectrode is particularly advantageous in enabling the detection and quantification of organic compounds in a water sample based on only a partial electrolytic decomposition of the organic compounds, as opposed to requiring a complete electrolytic decomposition of the organic compounds as in the case of a bulk boron-doped diamond electrode. In particular, as will be discussed further below, the use of a boron-doped diamond microelectrode enables a steady state response current to be rapidly achieved. Consequently, the aforementioned detection and quantification may be performed in a very short time frame of only a few seconds, as opposed to two or three hours or longer.

The boron-doped diamond microelectrode array of working electrode 15 may be formed from bulk boron-doped diamond in combination with a mask of a non-conducting silica layer, the aforementioned silica layer exposing a microarray of boron-doped diamond dots. The boron-doped diamond dots, which may number in the thousands (e.g., 10,000), may have a diameter in the range of about 5-50 μm and may have a spacing of about 50-500 μm. An example of a boron-doped diamond microelectrode array that may be suitable for use in the present invention is disclosed in Argun et al., "Highly sensitive detection of urinary cadmium to assess personal exposure," *Analytica Chimica Acta*, 773: 45-51 (2013), which is incorporated herein by reference.

Counter electrode 17 of probe 13 may comprise, for example, a graphite rod. Reference electrode 19 of probe 13 may comprise, for example, an Ag/AgCl miniature reference electrode.

System 11 may further comprise instrumentation to apply potential to the sensor and to measure sensor response. Such instrumentation may comprise a potentiostat 21. Connections from potentiostat 21 to electrodes 15, 17, and 19 may be made via wires 23, 25, and 27, respectively, which may be housed within a cable 29.

System 11 may further comprise instrumentation to convert sensor response to a determination of a quantity of electrochemically oxidizable organics present in a water sample. Such instrumentation may comprise, for example, a computer 31. Computer 31 may be coupled to potentiostat 21 via a cable 33.

As noted above, the method of detecting and quantifying organic compounds in a water sample in accordance with the present invention does not require the complete oxidation of the organic compounds contained therein. This is, in part, because the present invention employs a novel electrochemical technique that extracts relevant information from the sensed measurements and that analyzes such information to provide a result that can be correlated with COD standards. The discussion below provides some of the theoretical underpinnings of the present invention, as well as additional details as to how the present method may be practiced. It is to be understood that the present invention should not be limited by any theoretical basis or exemplary details provided herein.

Figure 2A:
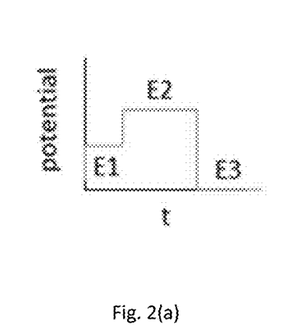
FIGS. 2(a) through 2(c) are graphic representations of a typical response to oxidation of organics directly related to (a) step voltage applied; (b) current-time response; (c) Anson plot (i.e., Q vs. $t^{1/2}$), respectively.
Figure 2B:
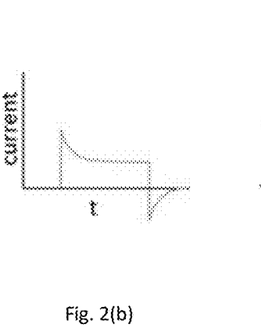

When voltage is applied instantaneously (e.g., a step change, such as from $E_1$ to $E_2$, as shown in FIG. 2(*a*)), the current rises instantaneously and then begins to drop as a function of time (FIG. 2(*b*)). As electrolysis proceeds, the reactant materials diffuse farther from the electrode; therefore, the concentration gradient for these materials drops. The measured current is related to the bulk reactant concentration and, for a diffusion-controlled current, can be described by the Cottrell equation:

$$i = \frac{nFCA\sqrt{D}}{\sqrt{(\pi t)}} \quad \text{Cottrell equation}$$

in which i represents current, n represents the number of electrons transferred/molecule, F represents Faraday's constant (96,500 C mol$^{-1}$), A represents the electrode area (cm$^2$), C represents concentration (mol cm$^{-3}$), D represents a diffusion coefficient (cm$^2$ s$^{-1}$), and t represents time.

Figure 2C:
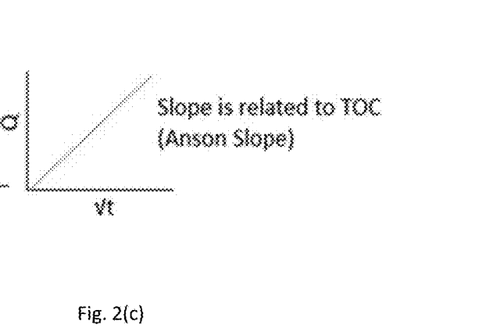

For example, the total charge (Q) that passes during the time following a potential step is measured as a function of time by integrating the current, i, during the potential step. For a well-behaved system (diffusion only), the charge observed following a potential step (FIG. 2(*c*)) is described by the integrated Cottrell equation, known as the Anson equation:

$$Q = \frac{2nFAC\sqrt{(Dt)}}{\sqrt{\pi}} \quad \text{Anson equation}$$

According to Faraday's Law, the mass of a substance altered at an electrode during electrolysis is directly proportional to the quantity of electricity transferred (charge) at that electrode. The quantity of electricity refers to the quantity of electrical charge, typically measured in Coulombs.

$$Q = \int_0^{tr} i(t)dt$$

In principle, organic compounds in an aqueous electrolyte can be oxidized, and the charge is proportional to the organic content according to the following derivation:

$$C_aH_bN_cO_d + yO_2 \rightarrow aCO_2 + \left(\frac{b}{2}\right)H_2O + cNO_2 \quad \text{(Eq. (1))}$$

($yO_2$ represents COD mg/L)

$$C_aH_bN_cO_d + \left(\frac{x-b}{2}\right)H_2O \rightarrow aCO_2 + cNO_2 + xH^+ + Xe^- \quad \text{(Eq. (2))}$$

The number of moles (m) of oxidized organic compound can be calculated according to the Faraday equation:

$$m = \frac{Q}{xF}$$

in which Q represents charge, F represents Faraday's constant, and x represents the number of electrons.

Comparing the electrochemical oxidation of organic compounds "$C_aH_bN_cO_d$" in an aqueous electrolyte at a highly positive potential as represented in Eq. (2) and comparing it with complete oxidation of the same organic compounds by reaction with oxygen as expressed in Eq. (1) through traditional COD measurements, one can develop a relationship between $yO_2$ (which represents COD) and x (the number of electrons transferred through electrolytic oxidation). Solving equations Eq. (1) and Eq. (2) yields $$x=4y \quad \text{(Eq. (3))}$$

Figure 3:
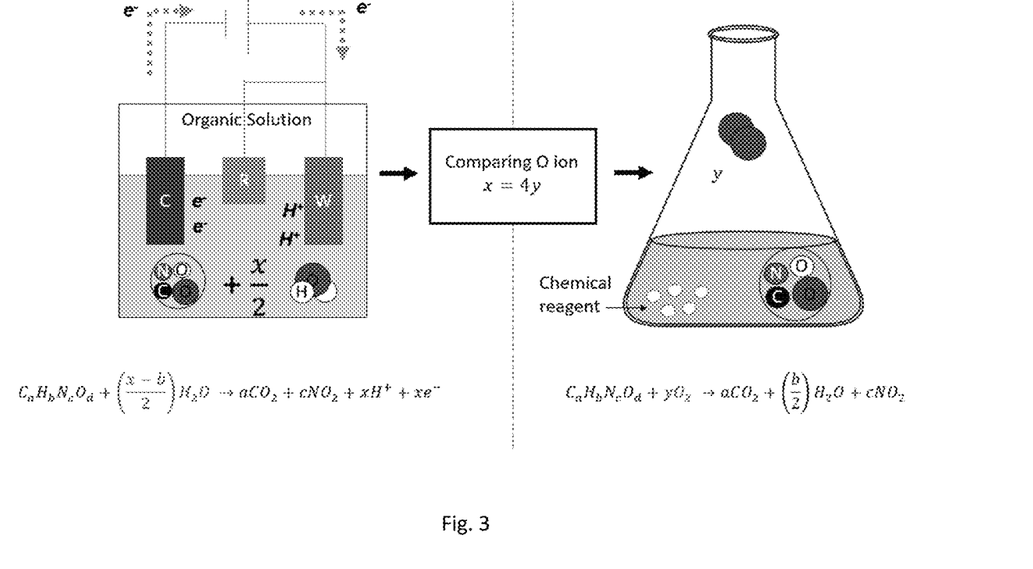
FIG. 3 is a schematic representation correlating eCOD electrolytic oxidation and COD techniques.

Therefore, the quantity of $O_2$ needed (which represents the traditional COD) is equivalent to ¼ times the number of electrons required to oxidize the same organic compound. Thus, the total charge for the electro-oxidation can be used to calculate the electrochemical oxygen demand (also referred to herein as eCOD or ECOD). FIG. 3 diagrammatically shows the relationship between electrochemical oxidation demand and chemical oxygen demand for the same amount of organics.

In electrochemistry, there is an important distinction between the concentration of a species at the surface of an electrode and its concentration at some distance away from the surface of the electrode (i.e., in the bulk solution); however, through sensor calibration, these two concentrations can be correlated. So, for example, if a species is oxidized at the electrode surface, the concentration at the electrode surface due to an electrode reaction is balanced by diffusion and related to the concentration in the bulk solution.

Therefore, in principle, by applying a highly oxidizing positive potential to an aqueous electrolyte containing a mix of organics for a short time, and by analyzing the current/charge corresponding to the electrolytic decomposition of the organic compounds, this measurement can be used to characterize the bulk solution constituents.

Consequently, there is no need to perform complete electrochemical oxidation, which takes a long time, in order to relate eCOD to COD. Instead, the key to the approach of the present invention is to perform quick controlled partial eCOD measurements for a short time, for example, less than about 4 seconds, which correlate to complete decomposition of organic compounds at a boron-doped diamond microelectrode. Provided below is an explanation as to why this is the case.

As discussed above and as seen in FIGS. 2(a)-2(c), the oxidation reaction becomes diffusion-limited after a given time. In evaluation of an unknown sample, the Cottrell equation contains three unknowns: n (the number of electrons transferred/molecule), C (concentration of reactant), and D (diffusion coefficient for reactant). To correlate current to nC (the number of electrons needed to fully oxidize the concentration of organic reactants present), D must be independently determined. However, by using a boron-doped diamond microelectrode array, D may be removed from consideration, thereby clearing the way for a direct correlation between current obtained and values translatable into COD values. This is because improved kinetics and hemispherical diffusion patterns are present when using a microelectrode. As a result, in the case of such a microelectrode, the Cottrell Equation becomes:

$$i(t) = \frac{X\sqrt{D}}{\sqrt{t}} + i_{ss}$$

Consequently, in the case of a microelectrode, the current response comprises a time-dependent term (i.e., the first term), which is dominant at small times, and a time-independent diffusion-limited term (i.e., the second term), which is dominant when time is sufficiently large for diffusion-limited oxidation to have been achieved. The specific equations that are applicable are related directly to diffusion patterns at microelectrodes of, but not limited to, the following geometries: spherical, cylindrical, micro-dots, etc. Specifically, in the case of a micro-disk of area $A=\pi a^2$, in which a is the radius of the micro-disk, the Cottrell equation may be expressed as follows:

$$i(t) = \frac{nFa^2\sqrt{(D\pi)}}{\sqrt{(t)}} + 4nFDCa$$

As such, the current is proportional to the diffusion coefficient (D), the number of electrons per molecule oxidized (n), and the concentration of those molecules oxidized (C). For a given solution, these are constants, but, in an unknown solution, the values of these constants are unknown. The value of nC (number of electrons per molecule multiplied by the concentration of these molecules) is directly proportional to the eCOD value. This leaves an unknown constant of diffusion coefficient (D) that must be found.

At large t, the steady state current is reduced to $i_{ss}=4nFDCA$. Therefore, by normalizing the current response to a potential step by the steady state current, D can be defined as a function of the slope (S2) of the $i/i_{ss}$ vs. $t^{-½}$ curve. (See Denault et al., "Direct determination of diffusion coefficients by chronoamperometry and microdisk electrodes," J. Electroanal. Chem., 308: 27-38 (1991), which is incorporated herein by reference.)

$$\frac{i}{i_{ss}} = \frac{a\sqrt{\pi}}{4\sqrt{D}}\left(\frac{1}{\sqrt{t}}\right) + 1$$

$$S2 = \frac{a\sqrt{\pi}}{4\sqrt{D}}$$

$$D = \frac{\pi a^2}{16(S2)^2}$$

Interpretation of the I vs. t, and Q vs. $t^{1/2}$ profile curves (FIGS. 2(b), and 2(c), respectively) provides insightful information about the anodic oxidation. For example, concentration can be derived from the Cottrell slope while the Anson slope can be used to define the charge-time dependence for linear diffusion control and to determine if there are any species being adsorbed on the working electrode (sensor).

Based on the above, the present invention encompasses two analysis techniques, which are discussed further below as Technique 1 and Technique 2. Techniques 1 and 2 may be used to obtain metrics that may be correlated with existing COD values and, in this manner, may be used to enable quantification of organics in a water sample.

Technique 1: Technique 1, which is used to obtain a Metric 1, comprises an analysis algorithm relating sensor response to potential steps to oxidizable organics. Integration of the Cottrell Equation provides the Anson Equation for a micro electrode (Eq. (4)). The Anson slope (Eq. (5)) is described by S1 at a micro-array of area $A=na^2$, the slope of the Q vs $\sqrt{t}$ plot.

$$Q = [2nCFa^2\sqrt{(\pi D)}]\sqrt{t} \quad \text{(Eq. (4))}$$

$$S1 = 2nCFa^2\sqrt{(\pi D)} \quad \text{(Eq. (5))}$$

By substituting D, which is found in the manner discussed above using the $i/i_{ss}$ technique, into Eq. (5), a direct relationship between these two slopes and "nC" can be found.

$$\frac{2}{\pi F a^3} S2 * S1 = nC \quad \text{(Eq. (6))}$$

The foregoing leads to a Metric 1 of S1*S2.

Technique 2: Technique 2, which is used to obtain a Metric 2, comprises an analysis algorithm in which the derivative of the Cottrell equation (Eq. (7)), again with micro-array area $A=\pi a^2$ and the slope S3 of the resulting di/dt vs. $t^{-3/2}$ curve (Eq. (8)) are used to provide a relationship between sensor response and COD (Eq. (9)).

$$\frac{di}{dt} = \left[\sqrt{\pi(D)} \, nCFa^2\right] t^{-\frac{3}{2}} \quad \text{(Eq. (7))}$$

$$S3 = \sqrt{\pi(D)} \, nCFa^2 \quad \text{(Eq. (8))}$$

$$\frac{S2 * S3}{nFa^3} = nC \quad \text{(Eq. (9))}$$

The foregoing leads to a Metric 2 of S2*S3.

To summarize the use of the metrics used in Technique 1 and Technique 2, both techniques reduce equations with two variables (nC and D) to one-variable equations to solve for nC. In each approach, two separate methods of finding a diffusion coefficient (D) are found, allowing for substitution to eliminate the variable D. S1 is the Anson slope and relates to the slope of Q vs $\sqrt{t}$. S2 uses unique diffusion patterns at a BDD micro-electrode to calculate D by normalizing current based upon the steady state, diffusion limited current, using the normalized current vs $1/\sqrt{t}$ curve. S3 relates to the rate of decay of the current response (di/dt) vs. $1/t^{1.5}$ to evaluate the diffusion coefficient. By equating the diffusion coefficient determined in any of these two ways, the variable D can be eliminated and thus the value nC, relating to the quantity of organics, can be determined.

Figure 4:
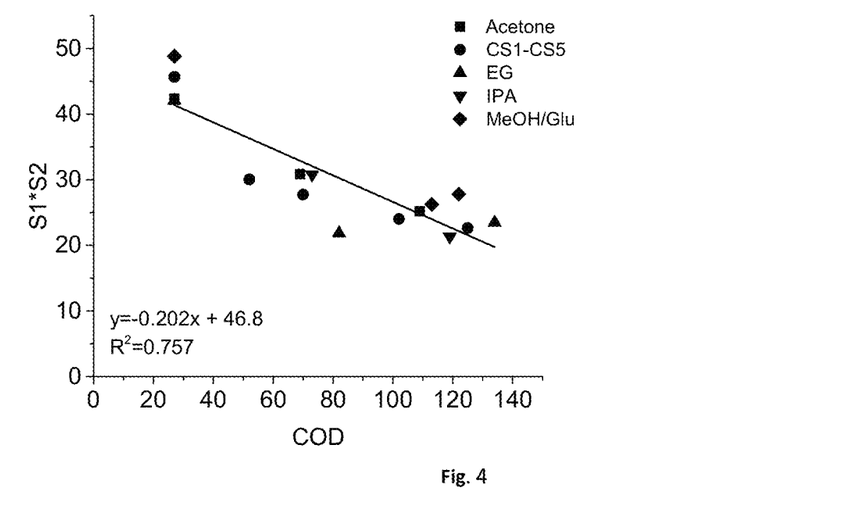
FIG. 4 is a graph depicting S1*S2 values obtained according to the present invention plotted against COD values for a variety of organic compounds spiked into a wastewater standard.
Figure 5:
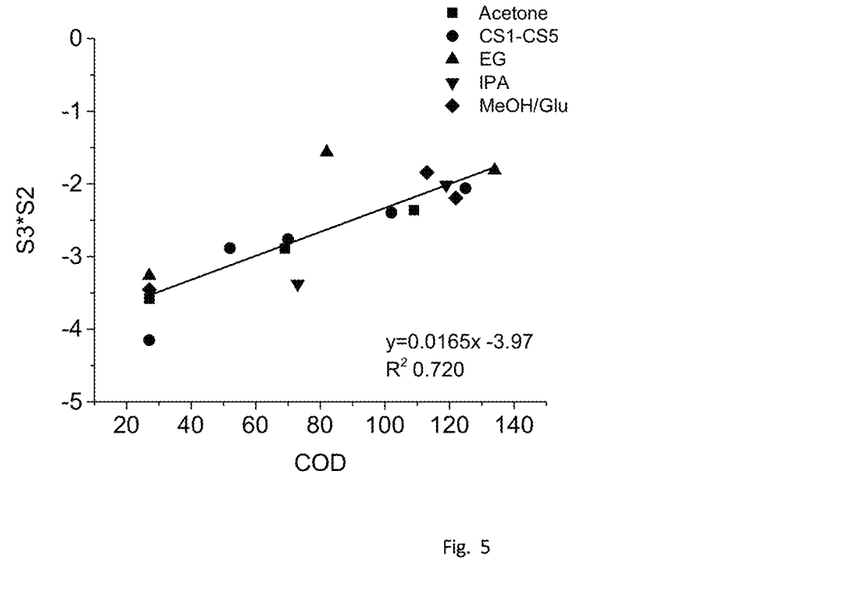
FIG. 5 is a graph depicting S2*S3 values obtained according to the present invention plotted against COD values for a variety of organic compounds spiked into a wastewater standard.

These two metrics (Metric 1 of S1*S2 and Metric 2 of S2*S3) have shown excellent and source-independent linear agreement with COD. Both were used to evaluate wastewater standard sets spiked with 5 different organic sources (Example 1 below). COD was confirmed by standard digestion methods. As shown in FIGS. 4 and 5, the sensor response is independent of source of organic.

In view of the above, a method for detecting and quantifying organic compounds in a water sample in accordance with the present invention may comprise, according to one embodiment, the following steps: (1) providing a system, the system comprising (a) a probe, the probe comprising a boron-doped diamond (BDD) microelectrode sensor; (b) instrumentation to apply potential to the sensor and to measure sensor response; and (c) instrumentation to convert sensor response to a determination of a quantity of electrochemically oxidizable organics present in the water sample; (2) submerging the sensor in the water sample; (3) applying a three-step voltage profile to the sensor, in which a first potential is applied for a first period of time, then a second potential, which is greater than the first potential, is applied for a second period of time, and then a third potential, which is less than the second potential, is applied for a third period of time; and (4) analyzing the current response to the three-step voltage profile. As noted above, the second period of time need only be applied for so long as needed to achieve a steady state current response. The analysis step may comprise using one or more of the metrics described above and, in particular, may comprise using such metrics to obtain a corresponding COD value. Accordingly, in practice of the present invention, both a set of COD standards and a set of correlations between eCOD and COD values may be obtained for standards obtained from a water source being evaluated. Then, with respect to a water sample whose organics content is unknown, one may use the present method to obtain a partial eCOD value, which can then be correlated with an existing COD value to determine the quantity of organics in the sample.

The above-described method may be regarded as a chronocoulometric (CC) method. Stirring need not be applied, and preferably is not applied, with this method.

The sensor assembly in the above-described chronocoulometric method may be submerged in the water sample of interest or in any dilution thereof. The voltage range which may be applied in the first, second and/or third steps may be any voltage in the range of approximately −1.0 V to 3.0 V vs. Ag/AgCl. In certain instances, the voltage applied in the second step may be 2-3 V, and, more particularly, may be 2.2-2.5 V. The period of time for the second step of the three-step voltage profile preferably corresponds to a time at which the current has stabilized (i.e., has reached a steady-state). This may be at any time from as soon as a few seconds or sooner up to a few minutes or longer after the second potential pulse has been applied. Preferably, this time will be within 4-5 seconds after the second potential pulse has been applied. The current response may then be adjusted to take into consideration the individual characteristics of the sample including, but not limited to, conductivity, pH, and temperature.

According to another aspect of the invention, a series of different potentials may be applied in the second step of the three-step profile, and the resulting corrected current responses may be compared to a library of known organic compound responses to provide additional information about not only the total amount of organic compounds in the sample but an identification of potential organic compounds that are present. A catalog of oxidation potentials for common water components can be devised by stepping through the second step potentials within a range from 0-3V to determine oxidation onset potential. The sensor of the present invention can then be used to identify a list of potential water components by testing water samples using a range of second step values from 0-3V and by comparing the onset potential of organics against the devised library.

Figure 6:
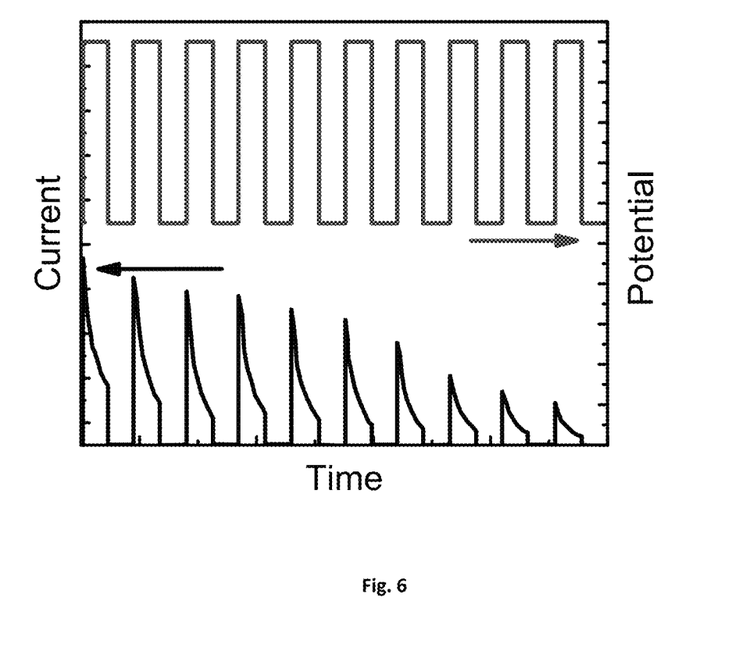
FIG. 6 is a set of voltage vs. time and current vs. time graphs, illustrating the use of multiple-steps of controlled-repeated potential in accordance with the enhanced chronocoulometric method of the present invention so as to enable COD/BOD measurements.

According to another aspect of the invention, an enhanced chronocoulometric (ECC) method may be employed in which the pulse utilized in the chronocoulometric method is repeated one or more times, and the response to the series of sequential pulses is used to improve the accuracy of the current response to COD conversion. To maximize device sensitivity and to obtain more consistent oxidation profiles, the use of the ECC method may be applied to an organic mix. The method may use multiple steps of controlled and repeated potential with specified times to create an oxidation profile. When the potential is stepped up to reach a point where oxidation takes place, the rate of change of current vs. time may be monitored. For example, a selected constant voltage step high enough to oxidize organics (i.e. 2.0-2.5 V range) may be used. Then, current decay and charge may be monitored as a function of time during the exhaustive electrolysis reaction (FIG. 6). This step may be repeated multiple times (shown 10 times in FIG. 6) and analysis may be performed for each step. The measured current (as well the area under the curve) may be reported from each region in the form of charge magnitude, current decay, Cottrell slope, Anson slope, etc. This measurement creates a large amount of information in the oxidation profile to assess water quality. In addition, this data provides useful important information about the quality of the waste stream and the affectivity of the electrochemical oxidation process and is to be used for mass balance and calculation of BOD and COD. The ECC measurement method is fast with a quick response (for example, performing 30 steps (one second on/off) interval may be done in one minute). This method can be used as a practical alternative to the classic, but lengthy, BOD and COD tests for determination of organics in aqueous solutions as the present technique can enable simple and rapid analysis.

It is to be understood that, although chronocoulometric methods are described above, the present invention is not limited to such methods and could include alternative methods, such as, but not limited to, chronoamperometric methods and cyclic voltammetry.

According to another embodiment of the invention, the organic oxidation response may be extracted and amplified. At low (<1000 μS) conductivity, sample conductivity can cause wide variations in current, which can complicate quantification of COD based upon the Anson slope (S1). One manner of addressing this problem in accordance with the present invention is to add one or more salts to the sample being tested. Such salts, which may include, but are not limited to, $MgSO_4$ may be added to the sample to produce a sufficiently high conductivity in a range of about 100 μS/cm to 100,000 μS/cm, preferably about 200 μS/cm to 10,000 μS/cm. By raising and controlling conductivity, a current response due to conductivity may be controlled and eliminated as a variable. Higher conductivity leads to significantly higher sensitivity (as defined by the slope of metric vs COD calibration curve), which improves accuracy.

Figure 7:
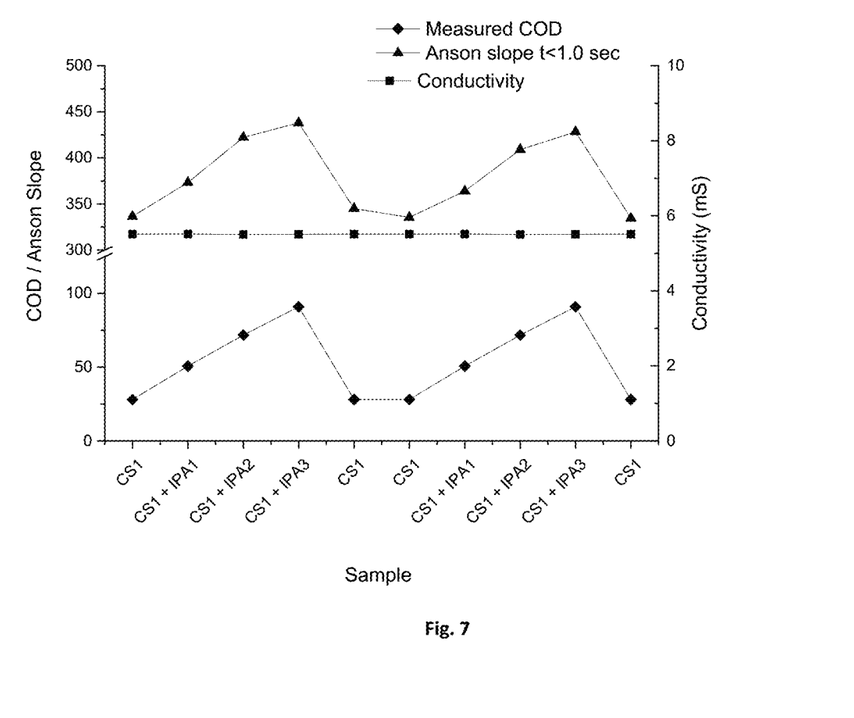
FIG. 7 is a graph depicting the relationship between COD values and Anson Slope (S1) values obtained according to the present invention at high (5.5 mS/cm) conductivity.
Figure 8:
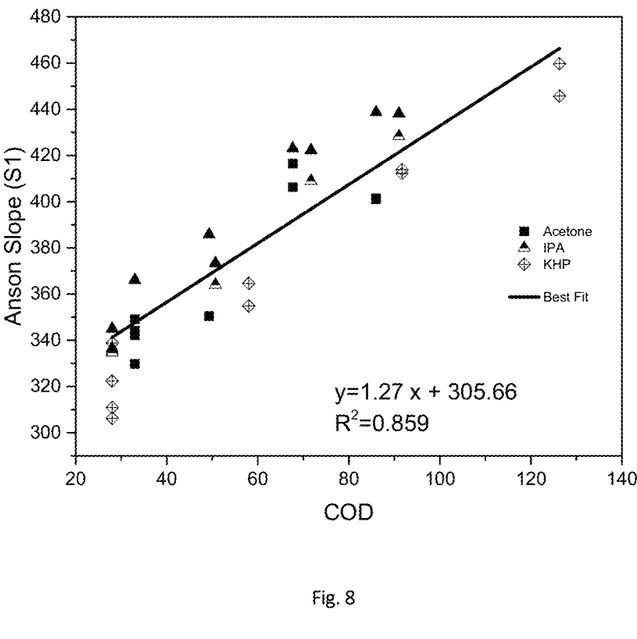
FIG. 8 is a graph depicting the relationship between COD values and Anson Slope (S1) values obtained according to the present invention, with conductivity controlled to 5.5 mS/cm for a number of different samples.
Figure 9:
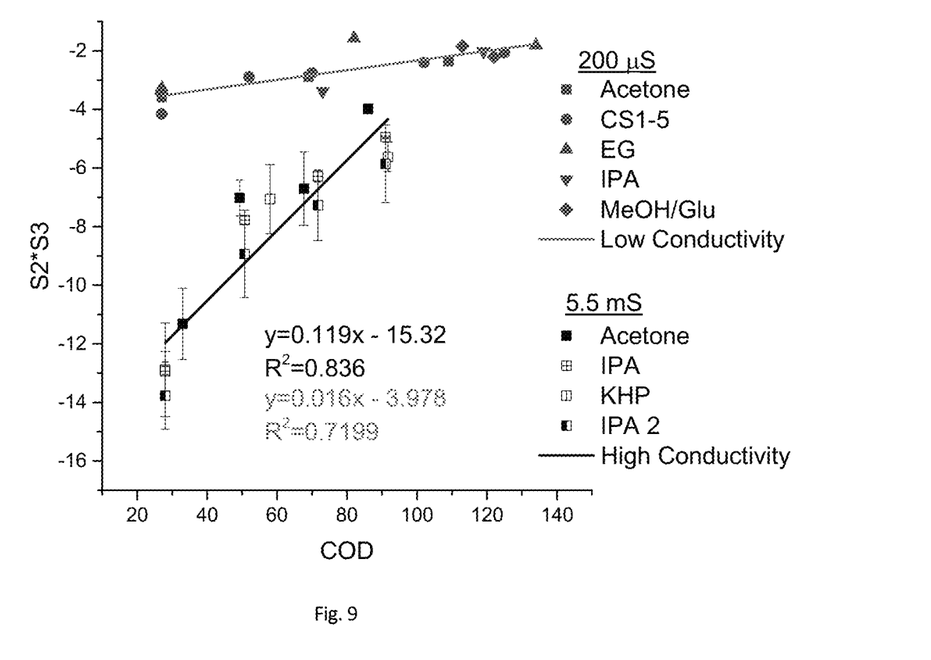
FIG. 9 is a graph depicting S2*S3 values obtained according to the present invention plotted against COD values for a variety of organic compounds in wastewater effluent at low (200 μS/cm) and high (5.5 mS/cm) conductivities.

At high conductivity, the Anson Slope (S1) is most closely correlated with COD. FIG. 7 shows a highly sensitive, clear, and repeatable sensor response to wastewater effluent (CS1) spiked with IPA. This response has been shown to be independent of organic, as shown in FIG. 8. While S1 response is well-defined at high conductivity, sensitivity to other low-conductivity metrics increases as well, as shown in FIG. 9. Increasing conductivity results in a 6.5× increase in sensor sensitivity to the same base (wastewater standard) with varying levels of organics present, as confirmed through a standard digestion method.

The present invention also may be used to distinguish BOD-related and COD-related signals for a given water sample. This may be done, according to one embodiment of the invention, by comparing the sensor response to a water sample before and after spiking the water sample with microorganisms capable of digesting organics present within the water sample. The measured reduction in signal (current) will only relate to the BOD component of the signal since the microorganisms will only convert organic matter that they can digest. This method does not rely on a full digestion of the organic species by the microorganisms, but rather, simply relates the signal from the sensor after partial digestion in a short time to the sample BOD.

Although the method of the present invention has been discussed above in the context of a batch process, it is to be understood that the present invention may also be used in the context of a continuous and inline process.

In summation, the present invention provides a low-cost, field-deployable, rapid, and real-time method that permits frequent monitoring of water samples. The present invention uses electrochemical oxidation profiling (i.e., current response) to characterize solution constituents and to assess water quality for management of pollution levels in a short time (e.g., seconds or minutes). The present invention is directly relatable to traditional COD measurements and can be used to distinguish biodegradable organic compounds from non-biodegradable organic compounds in a matter of minutes, not days. Moreover, the present invention does not involve the use or production of toxic heavy metals. Furthermore, in contrast with existing techniques, which are non-specific for different types of organic compounds, the present invention provides the capability of distinguishing between different organic compounds that may be present within the same water sample.

The following examples are provided for illustrative purposes only and are in no way intended to limit the scope of the present invention:

Example 1

Figure 10:
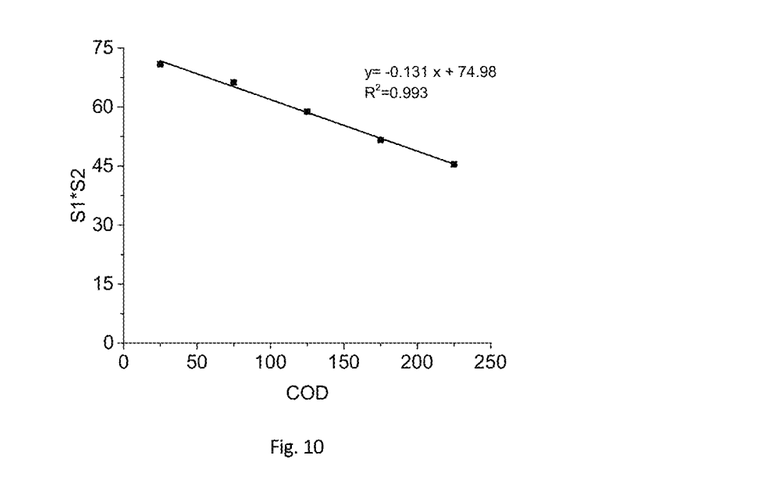
FIG. 10 is a graph depicting S1*S2 values obtained according to the present invention plotted against COD values for acetone spiked into a wastewater standard.
Figure 11:
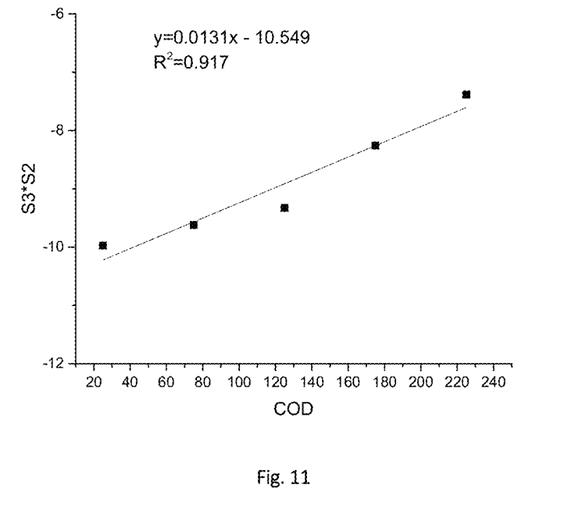
FIG. 11 is a graph depicting S2*S3 values obtained according to the present invention plotted against COD values for acetone spiked into a wastewater standard.

A commercially available wastewater effluent standard (COD 25, conductivity 200 uS, Hach Product #: 2833249) was obtained, and a spike solution of 1% acetone solution was prepared. 30 mL samples of the aforementioned effluent standard were prepared in separate vials and were spiked with 0 mL, 0.145 mL, 0.290 mL, 0.435 mL and 0.580 mL, respectively, of the aforementioned acetone spike solution, with COD confirmed by standard digestion method of 24 mg/L, 33 mg/L, 88 mg/L, 129 mg/L, and 154 mg/L, respectively. Double step chronocoulometry (CC method) was performed by applying 1.0 V for 0.5 seconds, then 2.5 V for 4.0 seconds, followed by 1.0 V for 0.5 seconds. For a calculation of S2, $i_{ss}$ was taken as the current at time t=4.5 seconds (the end of the 2.5 V potential step). Shown in FIG. 10 (Method 1) and in FIG. 11 (Method 2), both metrics are highly linear with COD measured by standard methods.

Acetone was chosen as a non-ionic organic to eliminate any influence of conductivity on current response.

Example 2

Figure 12:
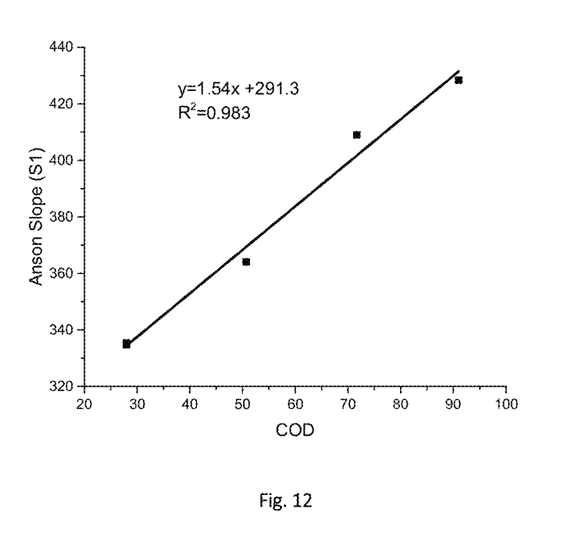
FIG. 12 is a graph depicting Anson Slope (51) values obtained according to the present invention plotted against COD values for isopropyl alcohol in a wastewater simulant at high conductivity.

A commercially available wastewater effluent standard (COD 25, conductivity 200 uS, Hach Product #: 2833249) was obtained, and a spike solution of 1% isopropyl alcohol (IPA) solution was prepared. The conductivity of a 210 mL volume of the aforementioned wastewater effluent was adjusted to 5.53 mS/cm by the addition of 2.2601 g of $MgSO_4*7H$. Four 30 mL samples were prepared from this adjusted base and spiked with 0 mL, 0.03975 mL, 0.0795 mL, and 0.11925 mL, respectively, of 1% IPA stock solution for final COD values of 28, 51, 72, and 91, respectively, confirmed with standard digestion method. Double step chronocoulometry (CC method) was performed by applying 1.0 V for 0.5 seconds, then 2.5 V for 4.0 seconds, followed by 1.0 V for 4.0 seconds. A plot of Anson slope vs. standard measurements of COD (FIG. 12) shows a clear linear relationship with excellent linearity and sensitivity of 1.54 S1 per mg/mLCOD.

Example 3

Figure 13:
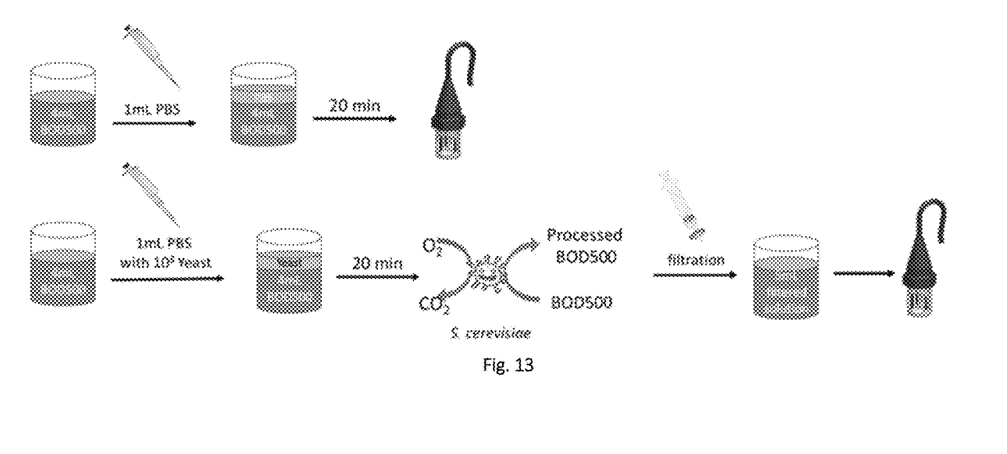
FIG. 13 is a schematic diagram depicting the method employed in Example 3.
Figure 14:
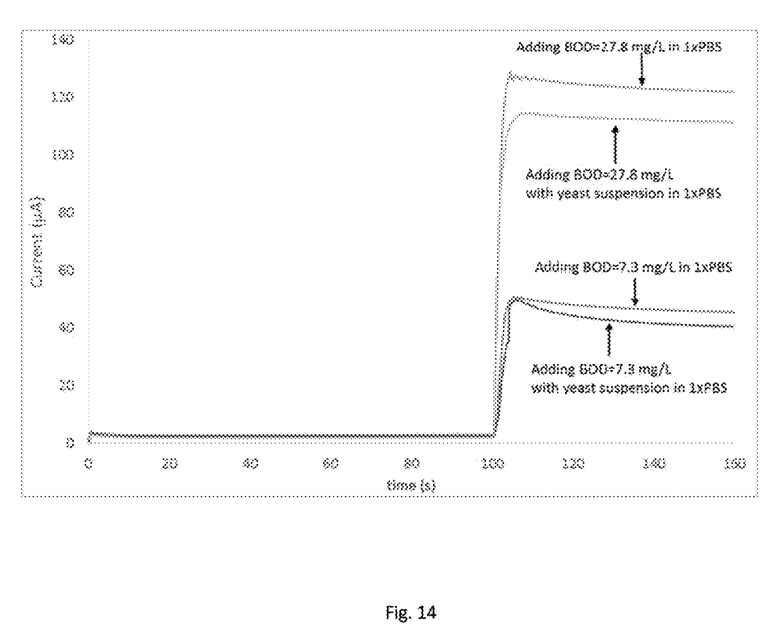
FIG. 14 is a graph depicting the chronoamperometry data obtained in Example 3 from both the control and test groups run after sitting for 20 minutes.

As shown in FIG. 13, 4 mL solutions of BOD500 simulants were prepared. These samples were then separated into two groups, with the first group (control group) receiving 1 mL of clean 0.1 M (1×) phosphate-buffered saline (PBS) and with the second group (test group) receiving 1 mL of 0.1 M (1×) PBS seeded with $10^8$ *S. cerevisiae* yeast cells. After the samples reached a 20-minute time limit and the yeast cells were removed, the samples were then run through a chronoamperometry analysis (see FIG. 14). The test ran for a total of 160 seconds at 2.7 V (vs. Ag/AgCl) in 3 mL of deionized (DI) water. The first 100 seconds were with DI water alone, and then either 56 μL or 224 μL of solution to be tested was added to the DI water to reach a BOD of 7 mg/L or 28 mg/L, respectively. The current difference was then calculated and plotted in FIG. 15.

Figure 15:
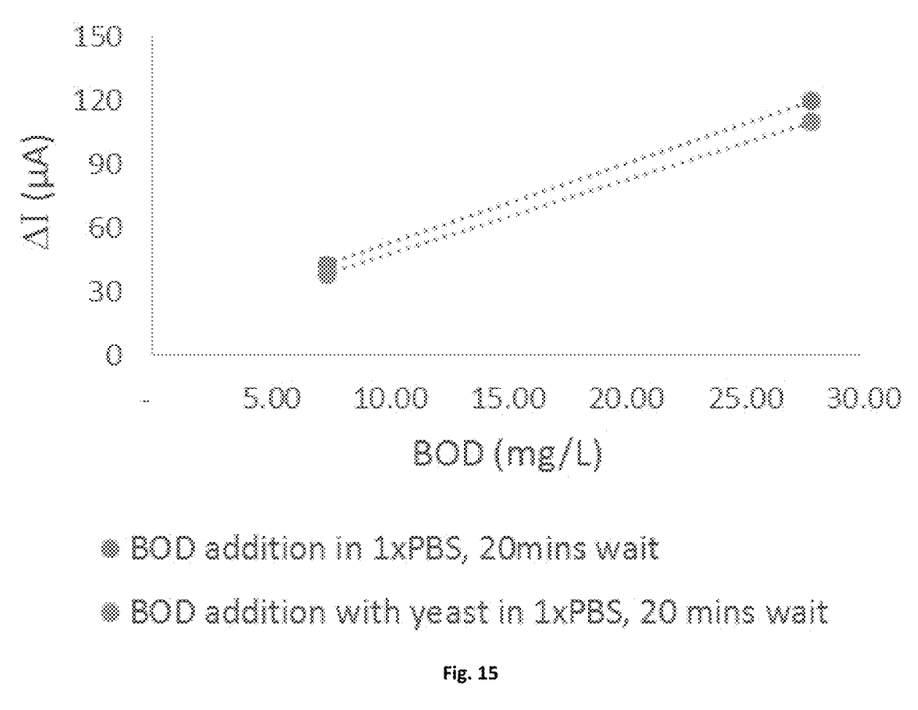
FIG. 15 is a graph depicting the current difference plotted against time for the two groups in Example 3.

As can be seen, there is about a 10% reduction in the current when yeast is added to the simulant, as compared to when no yeast was added. This reduction in current is an indicator that can be related only to BOD levels of the water being tested. In other words, the higher the original BOD loading, the greater the reduction in current that will occur.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for detecting and quantifying organic compounds in a water sample, the method comprising the steps of:
   (a) providing a system, the system comprising
      (i) a probe, the probe comprising a boron-doped diamond microelectrode sensor;
      (ii) instrumentation to apply potential to the boron-doped diamond microelectrode sensor and to measure a response of the boron-doped diamond microelectrode sensor to the applied potential; and
      (iii) instrumentation to convert the response of the boron-doped diamond microelectrode sensor to a value indicative of a quantity of electrochemically oxidizable organics present in the water sample;
   (b) inserting the boron-doped diamond microelectrode sensor into the water sample;
   (c) applying a voltage to the boron-doped diamond microelectrode sensor to only partially electrolytically decompose the oxidizable organics present in the water sample; and
   (d) analyzing the response of the boron-doped diamond microelectrode sensor to the applied voltage to yield a value indicative of the quantity of electrochemically oxidizable organics present in the water sample.

2. The method as claimed in claim 1 wherein the voltage is applied to the boron-doped diamond microelectrode sensor for at least as long as needed to elicit a steady-state current response from the boron-doped diamond microelectrode sensor.

3. The method as claimed in claim 2 wherein the voltage is applied to the boron-doped diamond microelectrode sensor as a three-step voltage profile, in which a first potential is applied for a first period of time, then a second potential, which is greater than the first potential, is applied for a second period of time, and then a third potential, which is less than the second potential, is applied for a third period of time.

4. The method as claimed in claim 3 wherein the second potential is applied for at least as long as needed to elicit a steady-state current response from the boron-doped diamond microelectrode sensor.

5. The method as claimed in claim 4 wherein the second potential is applied for no more than about 5 seconds.

6. The method as claimed in claim 4 wherein the analyzing step comprises determining at least one metric based on the response of the boron-doped diamond microelectrode sensor and comparing the at least one metric to chemical oxygen demand standards.

7. The method as claimed in claim 6 wherein the metric is slope of a charge vs. $t^{1/2}$ plot, wherein t is time.

8. The method as claimed in claim 6 wherein the metric is S1*S2, wherein S1 is slope of a charge vs. $t^{1/2}$ plot, wherein t is time, and wherein S2 is slope of an $i/i_{ss}$ vs. $t^{-1/2}$ curve, wherein i is current, $i_{ss}$ steady state current, and t is time.

9. The method as claimed in claim 6 wherein the metric is S2*S3, wherein S2 is slope of an $i/i_{ss}$ vs $t^{-1/2}$ curve, wherein i is current, $i/i_{ss}$ steady state current, and t is time, and wherein S3 is slope of a di/dt vs. $t^{-3/2}$ curve, wherein di/dt is rate of change of current and wherein t is time.

10. The method as claimed in claim 3 wherein the voltage applied in the second step is in a range of 0-3 V.

11. The method as claimed in claim 10 wherein the voltage applied in the second step is in a range of 2-3 V.

12. The method as claimed in claim 3 wherein a series of different potentials are applied in the second step of the three-step voltage profile to distinguish organic compounds present in the water sample.

13. The method as claimed in claim 1 wherein the boron-doped diamond microelectrode sensor comprises an array of boron-doped diamond microelectrodes.

14. The method as claimed in claim 13 wherein the array of boron-doped diamond microelectrodes comprises a plurality of boron-doped diamond microelectrodes having a diameter in the range of about 5-50 μm and having a spacing of about 50-500 μm.

15. The method as claimed in claim 1 wherein the probe further comprises a counter electrode and a reference electrode.

16. The method as claimed in claim 1 wherein the instrumentation to apply potential to the boron-doped diamond microelectrode sensor and to measure the response of the boron-doped diamond microelectrode sensor comprises a potentiostat and wherein the instrumentation to convert the response of the boron-doped diamond microelectrode sensor to a value indicative of a quantity of electrochemically oxidizable organics present in the water sample comprises a computer.

17. The method as claimed in claim 1 further comprising, before inserting the boron-doped diamond microelectrode sensor into the water sample, the step of adding salt to the water sample to produce a conductivity in the water sample in a range of about 100 µS/cm to 100,000 µS/cm.

18. The method as claimed in claim 1 further comprising repeating the applying and analyzing steps at least one time.

19. The method as claimed in claim 1 further comprising, after step (d), spiking the water sample with a quantity of an aerobic microorganism capable of digesting organic compounds, allowing the spiked water sample to sit for a period of time, re-inserting the boron-doped diamond microelectrode sensor into the spiked water sample in the event that it had previously been removed, then repeating steps (c) and (d) for the spiked water sample, and then comparing the values obtained before and after the water sample is spiked with the aerobic microorganism.

20. The method as claimed in claim 1 wherein the voltage is applied to the boron-doped diamond microelectrode sensor for at least as long as needed to elicit a steady-state current response from the boron-doped diamond microelectrode sensor and wherein the steady-state current response is attained within about 5 seconds.

* * * * *